United States Patent
Balestracci

(10) Patent No.: US 6,821,268 B2
(45) Date of Patent: Nov. 23, 2004

(54) TAMPER EVIDENT OVERAP OF A CONTAINER

(75) Inventor: Ernest Balestracci, Iselin, NJ (US)

(73) Assignee: Bracco Diagnostics Inc., Princeton, NJ (US)

(*) Notice: Subject to any disclaimer, the term of this patent is extended or adjusted under 35 U.S.C. 154(b) by 229 days.

(21) Appl. No.: 10/109,827

(22) Filed: Mar. 30, 2002

(65) Prior Publication Data

US 2003/0187403 A1 Oct. 2, 2003

(51) Int. Cl.$^7$ .......................... A61M 5/32; A61M 5/00
(52) U.S. Cl. ...................... 604/192; 604/110
(58) Field of Search .................. 604/110, 111, 604/187, 188, 192, 200, 201, 206, 212, 204, 240, 193, 194, 218, 263, 198, 197, 199, 232; 215/232, 250, 251, 252, 253; 220/257.1, 257.2, 377; 206/365

(56) References Cited

U.S. PATENT DOCUMENTS

| | | | |
|---|---|---|---|
| 4,171,699 A | * 10/1979 | Jones et al. | 604/187 |
| 4,758,230 A | * 7/1988 | Rycroft | 604/198 |
| 4,778,070 A | * 10/1988 | Walker | 215/232 |
| 4,886,497 A | 12/1989 | Scholl, Jr. | |
| 5,135,496 A | 8/1992 | Vetter et al. | 604/111 |
| 5,320,603 A | 6/1994 | Vetter et al. | 604/82 |
| 5,328,474 A | 7/1994 | Raines | |
| 5,615,772 A | 4/1997 | Naganuma | 206/365 |
| 5,624,402 A | 4/1997 | Imbert | |
| 5,678,718 A | * 10/1997 | Morris et al. | 220/254.1 |
| 5,709,659 A | * 1/1998 | Bennwik et al. | 604/110 |
| 5,785,691 A | 7/1998 | Vetter et al. | 604/187 |
| 5,902,298 A | 5/1999 | Niedospial et al. | |
| 6,027,482 A | 2/2000 | Imbert | 604/256 |
| 6,126,640 A | 10/2000 | Tucker et al. | 604/187 |
| 6,193,688 B1 | 2/2001 | Balestracci et al. | |

OTHER PUBLICATIONS

PCT Search Report For PCT/US03/09077 Mailed Sep. 23, 2003.

* cited by examiner

Primary Examiner—Manuel Mendez
(74) Attorney, Agent, or Firm—Caragh Noone Bryan Peckjian

(57) ABSTRACT

A tamper evident protective cap for a container having a pharmaceutical or biological fluid. The barrel of the container is equipped with two protuberances. The protective cap consisting of top and bottom portions are connected by a frangible portion. The bottom portion contains two notches to engage the protuberances. Without engaging the protuberances with the notches the protector cap cannot be removed. Upon engaging the protuberances with the notches, the top portion of the protective cap is twistably removed at the frangible area and the content of the container is removed by attaching a luer connector or a syringe equipped with a luer connector.

11 Claims, 4 Drawing Sheets

TAMPER EVIDENT OVERAP OF A CONTAINER

FIELD OF THE INVENTION

The present invention relates to a tamper evident protector overcap for a pre-filled syringe barrel. More particularly, the invention relates to a cap for a syringe barrel containing a liquid medication therein for securely holding a closure in the tapered tip of the syringe barrel and serving as a tamper evident indicator.

BACKGROUND OF THE INVENTION

Pre-filled syringe barrels or cartridges containing injectable solutions therein are stoppered by elastomeric closures, such as soft rubber stoppers at the distal, tapered end thereof, while the proximal end of the barrels are closed by slidable plungers. The pre-filled syringe barrels or cartridges are sterilized, such as by autoclaving, and packaged ready for use.

It has been observed that during in-line processing, handling, and sterilizing of the pre-filled barrels, some polymeric or elastomeric closures were missing from the tips of the barrels resulting in rejects. Also, during shipment of the finished product and handling by healthcare professionals some untipped barrels were observed which necessitated discarding of batches containing failed samples. For product integrity a corrective measure was indicated to prevent the polymeric or elastomeric closure from becoming dislodged from the tip of the barrel.

More importantly, it has also been recognized that untipped barrels, whether the damage occurred during shipment or handling, attracts the suspicion that the product was tampered with. Such possible tampering is a concern for both the National Regulating Authorities and the manufacturers who are required to insure safety, efficacy and the product integrity.

The prior art has provided various tamper evident closures for syringes.

For example, tamper evident syringes may be characterized in that the syringe barrel, the cap, and the plunger rod are covered with a tubular sealing device that is made from a heat-shrinkable film and which has been shrunk under heat so that it adheres closely to the surfaces of those members. The sealing device comprises a tube and a tear tape. The tube is formed of a transparent heat-shrinkable film. The tear tape is attached by bonding to the inner surface of the tube from one end to the other in the longitudinal direction.

Another example is a hypodermic syringe used with a needle for lyophilized medicament comprising: a syringe body having a piston therein equipped with a tip cap at its distal end; an elastomeric plug having a passage channel closing the neck of the syringe; and a protector cap which encloses the tip cap and the neck portion of the syringe body. The protector cap and tip cap are integral with each other and can be moved axially to open and close the syringe. The protector cap consists of a top portion and a bottom portion, the two parts being held together by a weakened portion. The center of the protector cap is provided with a small hole through which the tip cap can be viewed. In use, the top portion of the protector cap is snapped off at the weakened portion, and the tip cap is taken off and discarded. A needle is then fitted in the passage channel of the elastomeric plug to access the content of the syringe.

Still another example is discloses a syringe cap assembly placed on the distal end of a syringe. The assembly includes: an elastomeric insert having a passage therein; a retaining collar which fits over the elastomeric insert to hold the insert in place; a plug or tip cap is engaged in the insert to block the passage in the insert; and a retaining safety cap fitted over the tip cap. The end wall of the retaining safety cap is formed with a hole in its center and is slightly smaller in diameter than the plug so that the user can ascertain that the plug is properly in its place without opening the assembly.

In use the safety cap is pulled, twisted, and lifted off the assembly. The plug is then lifted off to expose the collar, and a needle assembly is fitted to the collar.

A further example is a pre-filled syringe with break-away tip seal which closes the passageway to the content of the syringe. A score means is provided adjacent to the tip for accommodating removal of the sealed tip.

An object of the present invention is to provide a pre-filled tamper evident syringe or cartridge barrel which makes apparent the unauthorized use of the medical fluid contained in the barrel of the syringe or cartridge or at least warns healthcare professionals that such unauthorized use may have occurred.

Another object of the present invention is to provide tamper evident syringe or cartridge barrels the content of which is easily accessed by the healthcare professionals while their unauthorized use is readily apparent.

A further object of the present invention is to provide a tamper evident syringe or cartridge barrel the content of which can be accessed by luer connections or a tubing conduit so as to avoid the use of "sharps" and thereby preventing needle stick injuries.

SUMMARY OF THE INVENTION

In accordance with the present invention, an overcap is provided for a syringe or cartridge barrel containing a pharmaceutical or biological liquid. The overcap is designed to indicate unauthorized use of the content of the syringe or cartridge barrel.

The pre-filled syringe or cartridge barrel terminates in a tapered tip having a bore therethrough. The tapered tip is equipped with a female luer connector to which a male luer connector or an injection needle may be attached. The bore in the tapered tip is stoppered by an elastomeric stopper, such as a soft rubber plug. At the base of the tapered tip above the shoulder of the syringe or cartridge barrel two protuberances or knobs are provided for engagement with cut-outs or notches in the overcap. A ring above the protuberances or knobs on the tapered tip serves to allow the overcap to turn in clockwise or counter-clockwise directions prior to disengaging the overcap from the syringe or cartridge barrel. The overcap covering the tapered tip comprises: a cylindrical top portion; and a cylindrical bottom portion. The cylindrical top and bottom portion may have the same diameter, or the bottom portion may have a slightly larger diameter than the top portion.

The top and bottom portions of the overcap are connected by a frangible area allowing the top portion to be removed from the bottom portion. The bottom portion in both embodiments is provided with cut-outs or notches designed to engage the protuberance or knobs on the distal end of the syringe or cartridge barrel.

In use, the healthcare practitioner depresses the overcap toward the barrel so that cut-outs or notches in the first embodiment, or cut-outs or notches in the second embodiment engage protuberances or knobs on the distal end of the barrel. Holding on to the top portion the overcap is twisted in clockwise or counter-clockwise direction so that the top portion is separated from the bottom portion at the frangible area between the top and bottom portions. The top portion is discarded while the bottom portion of the overcap remains on the distal end of the barrel. Next, the resilient closure is removed exposing the female luer connector to which a male luer connector or a syringe is attached for removal of the content of the barrel.

Separation of the top portion of the overcap from the bottom portion thereof prior to use indicates evidence to the healthcare professional that the product may have been tampered with and should not be used.

DETAILED DESCRIPTION OF THE INVENTION

Figure 1:
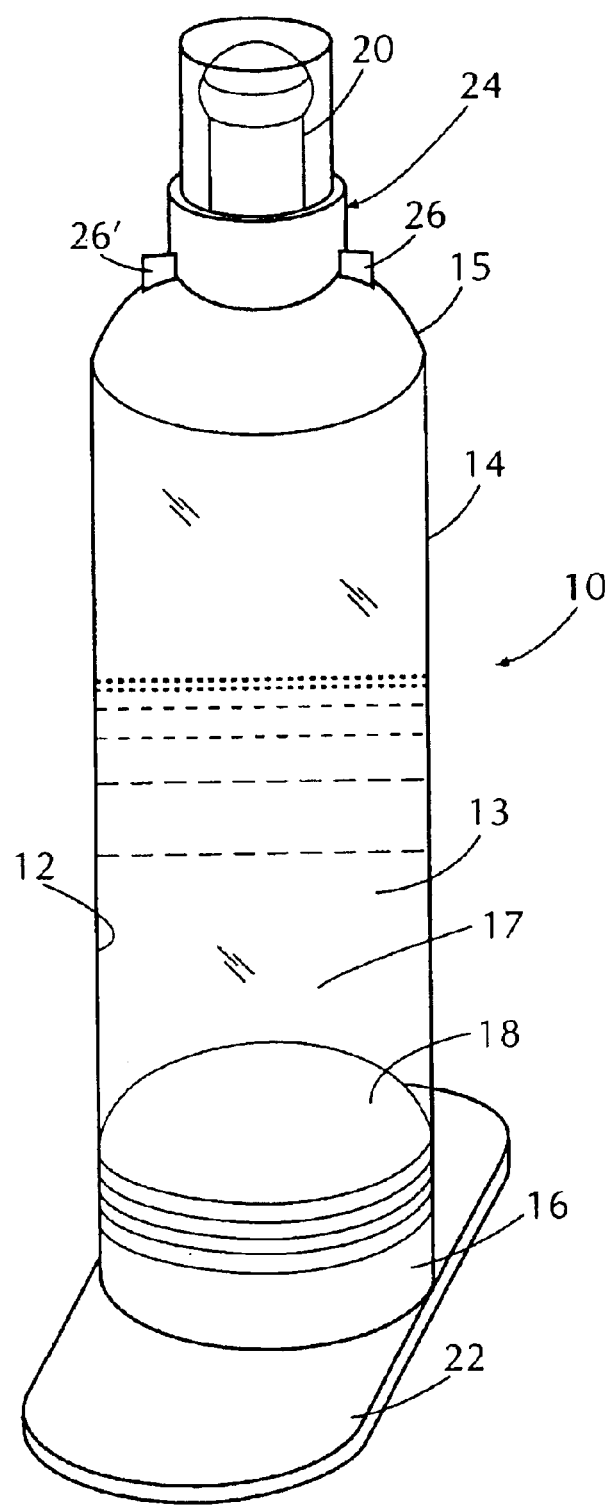
FIG. 1 is a perspective view of a syringe or cartridge barrel equipped with an overcap and containing a pharmaceutical or a biological liquid therein.
Figure 2:
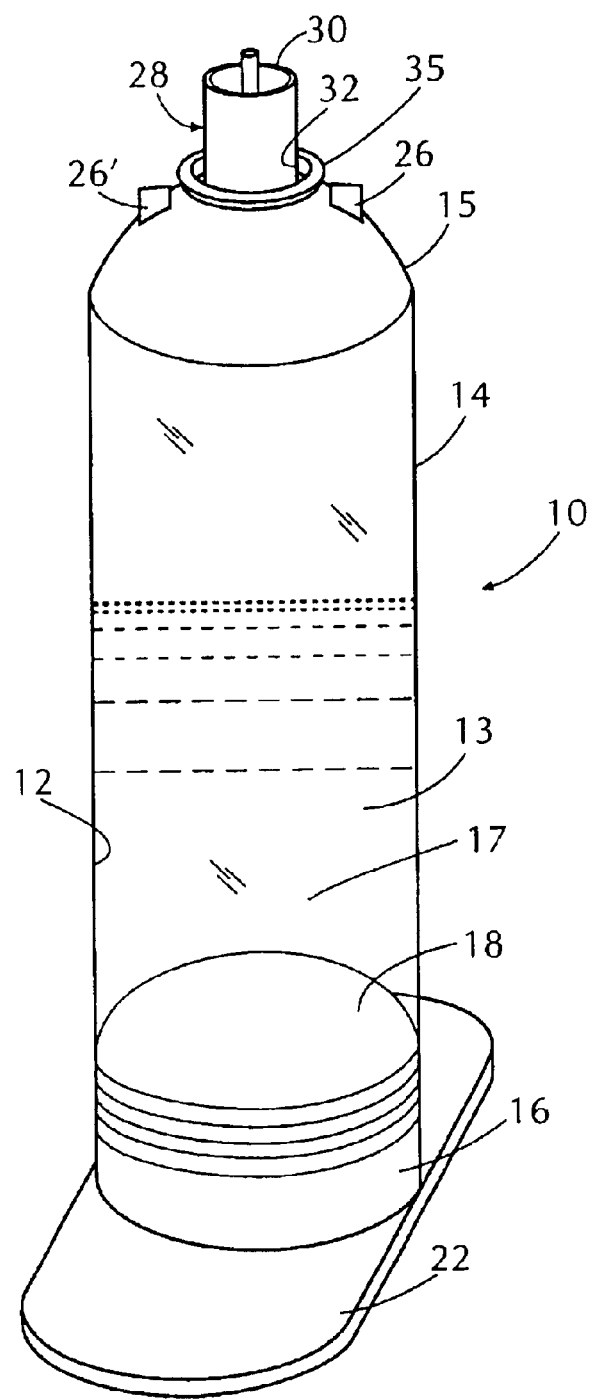
FIG. 2 is a perspective view of a syringe or cartridge barrel without an overcap and containing a pharmaceutical or a biological liquid therein.

FIGS. 1 and 2 show a syringe or cartridge barrel (hereinafter referred to as a barrel) in perspective views generally designated by the numeral 10 and an overcap generally designated by the numeral 24. FIG. 1 shows the barrel with the overcap, while FIG. 2 shows the barrel without the overcap.

The syringe or cartridge barrel, made of glass or a polymeric material, has an inner surface 12 defining a cylindrical chamber 13 for retaining a pharmaceutical or biological liquid 17 therein, such as a liquid x-ray contrast medium. The barrel has a distal end 14 terminating in a tapered tip 15 having a bore therethrough to which an injection needle or a luer connector with a tubing conduit can be attached, and a proximal end 16 for receiving a plunger 18 which retain the pharmaceutical or biological liquid in the barrel and which, upon use, expels the pharmaceutical or biological liquid from the barrel when an external pressure is exerted on the plunger. The tapered tip 15 having a bore therein is stoppered by a resilient closure 20, such as an elastomeric closure or a soft rubber stopper, for hermetically sealing the distal end of the barrel. At its proximal end 16 the barrel is equipped with an integral flange 22 to facilitate the handling of the overcap. When the pharmaceutical or biological liquid is an injectable solution, the barrel along with its content is sterilized, preferably by autoclave. After sterilization the barrel is packaged and stored ready for use when needed. Delivery of the injectable solution is accomplished by removing the overcap from the distal end of the barrel, and from the tapered tip of the barrel and attaching an injection needle or a luer connector onto the tapered tip of the barrel.

The barrel is equipped with two opposing protuberances or knobs 26 and 26' jutting out form the distal end 14 of the barrel adjacent to the tapered tip 15. The function of these protuberances or knobs will be pointed out as the description of the invention proceeds.

The tapered tip 15 of the barrel terminates in a typical female luer connector 28, generally designated, for attachment of a male luer connector or an injection needle thereto. The luer connector is integral with the tapered tip of the barrel and comprises an open distal end 30, and a closed proximal end 32. At the proximal end of the female luer connector and spaced from protuberance or knobs 26 and 26', there is provided a ring 35 surrounding the female luer connector 28. The outside diameter of the ring is slightly smaller than the inside diameter of the overcap thereby allowing turning of the overcap either in clockwise or counter-clockwise direction.

FIGS. 3, 4, 5 and 6 shows the overcap, generally designated at 24, in various views.

Figure 3:
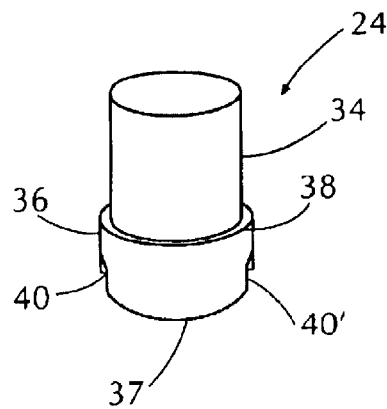
FIG. 3 is a perspective view of an overcap constituting one embodiment of the present invention.

FIG. 3 is a perspective view of the overcap comprising: a top portion 34, and a bottom portion 36 separated by a frangible portion 38. The bottom portion has a slightly larger diameter than the top portion. The proximal end 37 of the bottom portion is provided with two cut-outs or notches 40 and 40' on opposite sides of the bottom portion. The notches are designed to engage protuberances or knobs 26 and 26' at the distal end of the barrel.

Figure 4:
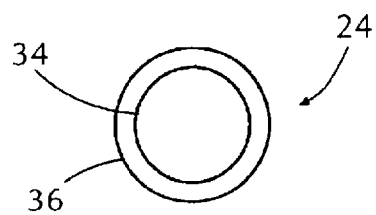
FIG. 4 is a top plan view of the overcap shown in FIG. 3.

FIG. 4 shows a top plan view of the overcap 24 having top portion 34 and bottom portion 36.

Figure 5:
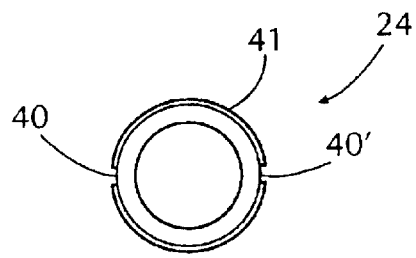
FIG. 5 is a bottom plan view of the overcap shown in FIG. 3.

FIG. 5 shows a bottom plan view of the overcap 24 having cut-outs or notches 40 and 40' on opposite sides of the bottom portion 36. The bottom portion further comprises a rim or flange 41 extending inward from the proximal end 37, except it lacks continuity at cut-outs or notches 40 and 40', The height of rim 41 is larger than the height of the ring 35 on the barrel so that the overcap 24 cannot be removed from the barrel without other manipulations described later in the process of using the overcap in preventing unauthorized use of the content of the barrel.

Figure 6:
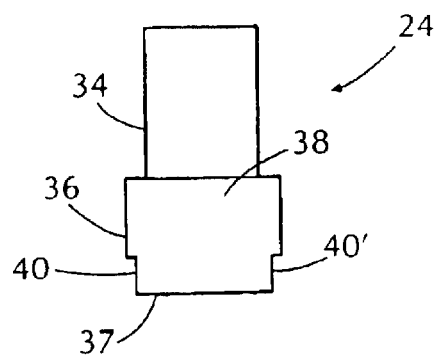
FIG. 6 is a side-elevational view of the overcap shown in FIG. 3.

FIG. 6 shows a side-elevational view of the overcap 24 comprising: top portion 34, bottom portion 36 which are separated by a frangible portion 38. The proximal end 37 is provided with two cut-outs or notches 40 and 40' on opposite sides of the bottom portion. The notches are designed to engage protuberances or knobs 26 and 26' at the distal end of the barrel.

FIGS. 7, 8, 9 and 10 show another embodiment of the overcap, generally designated at 42, in various views. Unlike the previously described overcap wherein the bottom portion has a slightly larger diameter as compared to the diameter of the top portion, in this embodiment the diameters of the bottom and top portions of the overcap are the same.

Figure 7:
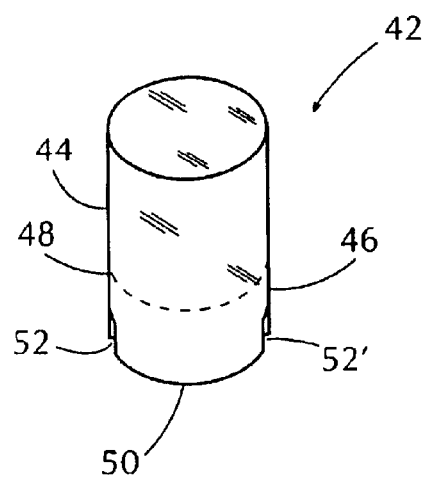
FIG. 7 is a perspective view of an overwrap constituting another embodiment of the present invention.

FIG. 7 is a perspective view of the overcap comprising: a top portion 44, and a bottom portion 46 separated by a frangible portion 48. The proximal end 50 of the bottom portion is provided with two cut-outs or notches 52 and 52' on the opposite sides of the bottom portion. The notches are designed to engage protuberances or knobs 26 and 26' at the distal end of the barrel.

Figure 8:
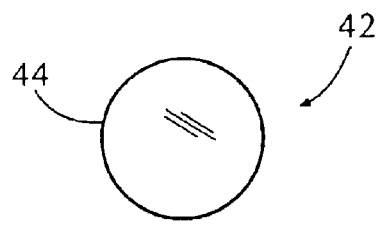
FIG. 8 is a top plan view of the overcap shown in FIG. 7.

FIG. 8 shows a top plan view of the overcap 42 in which top portion 44 and bottom portion 46 have the same diameter.

Figure 9:
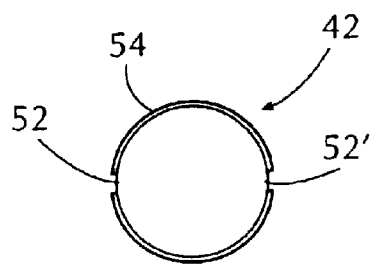
FIG. 9 is a bottom plan view of the overcap shown in FIG. 7.

FIG. 9 shows a bottom plan view of the overcap 42 having cut-outs or notches 52 and 52' on opposite sides of the bottom portion 46. The bottom portion further comprises a rim or flange 54 extending inward from the proximal end 50, except it lacks continuity at cut-outs or notches 52 and 52'. The height of rim or flange 54 is larger than the height of the ring 35 on the barrel so that the overcap 42 cannot be removed from the barrel without other manipulations described later in the process of using the overcap in preventing unauthorized use of the content of the barrel.

Figure 10:
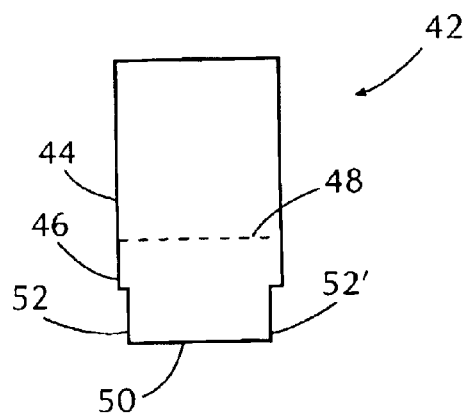
FIG. 10 is a side-elevational view of the overcap shown in FIG. 7.

FIG. 10 shows a side-elevational view of the overcap 42 comprising: top portion 44 and bottom portion 46 which are separated by a frangible portion 46. The diameters of the top and bottom portions are equal. The proximal end 50 is provided with two cut-outs or notches 52 and 52' on opposite sides of the bottom portion. The notches are designed to engage protuberances or knobs 26 and 26' at the distal end of the barrel.

The overcaps 24 and 42, respectively in the two embodiments of the present invention, may be made of a polymeric material including but not limited to: polyolefins such as polyethylene and polypropylene; polystyrene, polycarbonate, polymethylpentene, cyclic olefin co-polymers, acrylic polymers and methacrylic polymers.

Both embodiments of the present invention are used with pre-filled barrels containing, for example, a biological liquid or a pharmaceutical such as contrast media. Subsequent to the pre-fill the overcap is positioned on the distal end of the barrel, such as by crimping the overcap onto the distal end of the barrel. The rim or flange 41 or 54 respectively are pressed and forced to slide over the ring 35 to be placed in position over the distal end of the barrel. The content of the barrel is sterilized with traditional means, such as autoclaving.

When the overcap is positioned over the distal end of the barrel, it may be turned clockwise or counter-clockwise without resulting in the removal of the overcap. Personnel not familiar with the proper removal procedure will not be able to remove the overcap. The proper removal of the overcap is as follows: the overcap is pressed down towards the barrel until the cut-outs or notches 40 and 40' or 52 and 52', respectively, engage protuberances or knobs 26 and 26' on the distal end of the barrel. Upon such engagement the overcap will not turn either clockwise or counter-clockwise direction. The top portion of the overcap 34 and 44 respectively, is then turned clockwise or counter-clockwise to separate the top portions from the bottom portions 36 and 46, respectively. The frangible portions 38 and 48, respectively, allow such separation of the top and bottom portions. While the bottom portions remain on the distal end of the barrel, the top portions are removed to expose the resilient closures 20 upon the removal of which the female luer connector 28 is exposed. To the female luer connector a male luer connector, having an injection needle or IV tubing, is attached for withdrawal of the content of the barrel.

It is to be noted that upon separation of the top portion of the overcap from the bottom portion thereof along the frangible portion therebetween, the two portions cannot be reconnected without notice by the healthcare practitioner. If the overcap is tampered with, the healthcare professional will readily observe the separated top and bottom portions of the overcap along the frangible portion therebetween. As a result of this tamper evidence the content of the barrel will not be used.

While the present invention has been described in combination with a pre-filled syringe or cartridge barrel, it may be used in combination with other pre-filled containers such as tubes and bottles.

PARTS LIST

Syringe or cartridge barrel, generally designated 10
Overcap, generally designated 24
Inner surface of syringe or cartridge barrel 12
Cylindrical chamber of syringe or cartridge barrel 13
Pharmaceutical or biological liquid 17
Distal end of barrel 14
Tapered tip of barrel 15
Proximal end of barrel 16
Plunger 18
Resilient closure 20
Integral flange of barrel 22
Protuberances or knobs at distal end of barrel 26, 26'
Female luer connector, generally designated 28
Open distal end of female luer connector 30
Closed proximal end of female luer connector 32
Top portion of overcap 34
Ring on distal end of the barrel 35
Bottom portion of overcap 36
Proximal end of bottom portion 37
Frangible area between top and bottom portions of overcap 38
Cut-outs or notches in the proximal end of the bottom portion 40, 40'
Rim or flange in bottom portion 41
Overcap, generally designated 42
Top portion of overcap 44
Bottom portion of overcap 46
Frangible area between top and bottom portions of overcap 48
Proximal end of bottom portion 50
Cut-outs or notches in the proximal end of bottom portion 52, 52'
Rim or flange in bottom portion 54

Various modifications of the present invention disclosed will become apparent. This invention is intended to include such modifications to be limited only by the scope of the claims.

What is claimed is:

1. A combination of a tamper evident protective cap and a pre-filled glass or plastic syringe or cartridge barrel or a tube stoppered by an elastomeric closure at its tapered distal end wherein said syringe or cartridge barrel or tube comprises:

a) a cylindrical chamber having a tapered distal end terminating in a tip having a bore therethrough, said bore is stoppered by an elastomeric closure, said cylindrical chamber containing a liquid therein, wherein said tip is equipped with a female luer connector to which a male luer connector may be attached;

b) a pair of protuberances at the tapered distal end on the opposite sides of the barrel designed to receive and engage a pair of notches on the proximal end of a tamper evident protective cap;

c) a ring on the tapered distal end of the barrel spaced between said pair of protuberances and said female luer connector;

d) wherein said tamper evident protective cap is removably engaged with said tapered distal end of said syringe or cartridge barrel or tube and comprises:
      a cylindrical top portion and a cylindrical bottom portion connected by a frangible area allowing the top portion to be removed from the bottom portion, wherein: said cylindrical top portion terminates in a flat circular surface conforming to said elastomeric closure in said tip of the syringe or cartridge barrel or tube; said bottom portion terminates in an open end comprising a flange extending inwardly designed to engage the ring such that the engagement prevents removal of the tamper evident protective cap; and a pair of notches on the proximal end of said tamper evident protective cap engaging said pair of protuberances on the tapered distal end of the syringe or cartridge barrel or tube, wherein upon engagement of said pair of notches with said pair of protuberances on the top portion of said tamper evident protecting cap is twistably separated from the bottom portion thereof thereby exposing the tapered tip along with the elastomeric closure and female luer connector ready for withdrawal of said liquid from said syringe or cartridge barrel or tube.

2. The combination of a tamper evident protective cap and a pre-filled glass or plastic syringe or cartridge barrel or a tube of claim 1 wherein said cylindrical bottom portion is slightly larger than said cylindrical top portion and separated by said frangible portion therebetween.

3. The combination of a tamper evident protective cap and a pre-filled glass or plastic syringe or cartridge barrel of a tube of claim 1 wherein said cylindrical bottom portion and said cylindrical top portion are of the same size separated by said frangible portion therebetween.

4. The combination of a tamper evident protective cap and a pre-filled glass or plastic syringe or cartridge barrel or a tube of claim 1 wherein said ring on the tapered distal end of the barrel prevents removal of said tamper evident protective cap prior to separation of said bottom and top portions of said tamper evident protective cap.

5. The combination of a tamper evident protective cap and a pre-filled glass or plastic syringe or cartridge barrel or a tube of claim 1 wherein said tamper evident protective cap is made of a polymer material selected from the group consisting of polyethylene, polypropylene, polystyrene, polycarbonate, polymethylpentene, cyclic olefin co-polymers, acrylic polymers and methacrylic polymers.

6. The combination of a tamper evident protective cap and a pre-filled glass or plastic syringe or cartridge barrel or a tube of claim 1 wherein said liquid in said syringe or cartridge barrel or tube is a pharmaceutical or biological liquid.

7. The combination of a tamper evident protective cap and a syringe or cartridge barrel or a tube of claim 6 wherein said pharmaceutical or biological liquid is sterilized.

8. The combination of a tamper evident protective cap and a pre-filled syringe or cartridge barrel or a tube of claim 7 wherein said sterilization is by autoclave.

9. The combination of a tamper evident protective cap and a pre-filled syringe or cartridge barrel or a tube of claim 1 wherein said elastomeric closure is a soft rubber stopper.

10. A method of delivering a pharmaceutical or biological liquid to a patient from a pre-filled glass or plastic syringe or cartridge barrel or tube equipped with a tamper evident protective cap comprising providing a combination of a tamper evident protective cap and a pre-filled syringe or cartridge barrel or tube, wherein said delivery comprises the steps of:

A) providing a glass or plastic syringe or cartridge barrel or tube containing a pharmaceutical or biological liquid therein, said syringe or cartridge barrel or tube comprising:
  a) a cylindrical chamber having a tapered distal end terminating in a tip having a bore therethrough, said bore is stoppered by an elastomeric closure, wherein said tip is equipped with a female luer connector to which a male luer connector is attached;
  b) a pair of protuberances at the tapered distal end on the opposite sides of the barrel designed to receive and engage a pair of notches on the proximal end of a tamper evident protective cap;
  c) a ring on the tapered distal end of the barrel spaced between said pair of protuberances and said female luer connector;
  d) wherein said tamper evident protective cap is removably engaged with said tapered distal end of said syringe or cartridge barrel or tube and comprises:
    a cylindrical top portion and a cylindrical bottom portion connected by a frangible area allowing the top portion to be removed from the bottom portion, wherein: said cylindrical top portion terminates in a flat circular surface conforming to said elastomeric closure in said tip of the syringe or cartridge barrel or tube; said bottom portion terminates in an open end comprising a flange extending inwardly designed to engage the ring such that the engagement prevents removal of the tamper evident protective cap; and a pair of notches on the proximal end of said tamper evident protective cap engaging said pair of protuberances on the tapered distal end of the syringe or cartridge barrel or tube, wherein upon engagement of said pair of notches with said pair of protuberances on the top portion of said tamper evident protecting cap is twistably separated from the bottom portion thereof thereby exposing the tapered tip along with the elastomeric closure and female luer connector ready for withdrawal of said liquid from said syringe or cartridge barrel or tube;

B) engaging said pair of notches with said pair of protuberances on the top portion of said tamper evident protective cap;

C) separating said top portion from said bottom portion of the protecting cap by twisting thereby exposing the tapered tip along with the elastomeric closure and female luer connector;

D) removing the elastomeric closure from the tip of the syringe or cartridge barrel or tube;

E) connecting a male luer connector or a syringe equipped with a male luer connector to the female luer connector; and F) delivering the pharmaceutical or biological liquid to the patient by advancing a plunger in said syringe or cartridge barrel or tube towards the distal end thereof.

11. The method of claim 10 wherein said pharmaceutical or biological liquid is an x-ray contrast medium.

* * * * *

UNITED STATES PATENT AND TRADEMARK OFFICE
CERTIFICATE OF CORRECTION

PATENT NO. : 6,821,268 B2
DATED : November 23, 2004
INVENTOR(S) : Ernest Balestracci It is certified that error appears in the above-identified patent and that said Letters Patent is hereby corrected as shown below:

Title page,
Item [54], Title, should read
-- [54] Title: TAMPER EVIDENT OVERLAP FOR A CONTAINER --

Signed and Sealed this

Twenty-fourth Day of May, 2005

JON W. DUDAS
*Director of the United States Patent and Trademark Office*

UNITED STATES PATENT AND TRADEMARK OFFICE
CERTIFICATE OF CORRECTION

PATENT NO.       : 6,821,268 B2  Page 1 of 1
APPLICATION NO. : 10/109827
DATED            : November 23, 2004
INVENTOR(S)      : Ernest Balestracci It is certified that error appears in the above-identified patent and that said Letters Patent is hereby corrected as shown below:

Title page,
Item [54], Title, should read
-- [54] Title: TAMPER EVIDENT OVERCAP FOR A CONTAINER --

This certificate supersedes Certificate of Correction issued May 24, 2005.

Signed and Sealed this

Second Day of January, 2007

JON W. DUDAS
*Director of the United States Patent and Trademark Office*